(12) United States Patent
Landry et al.

(10) Patent No.: US 11,357,872 B2
(45) Date of Patent: Jun. 14, 2022

(54) IMAGING NEUROTRANSMITTERS IN VIVO USING FUNCTIONALIZED CARBON NANOTUBES

(71) Applicant: The Regents of the University of California, Oakland, CA (US)

(72) Inventors: Markita P. Del Carpio Landry, Berkeley, CA (US); Linda A. Wilbrecht, Berkeley, CA (US); Jackson Travis Del Bonis-O'Donnell, Berkeley, CA (US); Abraham G. Beyene, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 20 days.

(21) Appl. No.: 16/917,915

(22) Filed: Jul. 1, 2020

(65) Prior Publication Data

US 2020/0330614 A1 Oct. 22, 2020

Related U.S. Application Data

(60) Division of application No. 16/373,542, filed on Apr. 2, 2019, now abandoned, which is a continuation of application No. PCT/US2017/055995, filed on Oct. 10, 2017.

(60) Provisional application No. 62/405,963, filed on Oct. 9, 2016.

(51) Int. Cl.
| | |
|---|---|
| *A61K 49/00* | (2006.01) |
| *B82Y 5/00* | (2011.01) |
| *B82Y 15/00* | (2011.01) |
| *G01N 33/94* | (2006.01) |
| *B82Y 30/00* | (2011.01) |

(52) U.S. Cl.
CPC ............ *A61K 49/0054* (2013.01); *B82Y 5/00* (2013.01); *B82Y 15/00* (2013.01); *G01N 33/9406* (2013.01); *B82Y 30/00* (2013.01); *Y10S 977/75* (2013.01); *Y10S 977/92* (2013.01); *Y10S 977/927* (2013.01)

(58) Field of Classification Search
CPC ...... A61K 49/0054; B82Y 5/00; B82Y 15/00; G01N 33/9406; Y10S 977/927; Y10S 977/92
See application file for complete search history.

*Primary Examiner* — James W Rogers
(74) *Attorney, Agent, or Firm* — Richard Aron Osman

(57) ABSTRACT

Imaging based detection of changes in extracellular neurotransmitter concentration in living tissue is achieved using novel nanotube-based sensors. The sensors are functionalized, neurocompatible single-walled carbon nanotubes (SWNT) comprising an adsorbed neurotransmitter analyte selective polynucleotide.

20 Claims, No Drawings

IMAGING NEUROTRANSMITTERS IN VIVO USING FUNCTIONALIZED CARBON NANOTUBES

INTRODUCTION

Neurotransmitters play a central role in complex neural networks by serving as chemical units of neuronal communication. As a result, spatiotemporal neurotransmitter sensing has the potential to profoundly impact on our understanding of how the brain works, and presents a new platform by which to validate the function of neurological drugs. Therapeutic drugs that target neurotransmitter release are used ubiquitously to treat a vast array of brain and behavioral disorders: for over 60 years, drugs that alter, mimic, or block dopamine have formed the core arsenal for the treatment of neurological disorders such as depression, addiction, schizophrenia, anxiety, Parkinson's disease, and social autism spectrum disorder. However, currently in neuroscience, few analytical methods exist that can detect neurotransmitters with high spatial and temporal resolution in vivo in extracellular space. The difficulty of in vivo analyte detection emanates from the optical density of the brain, and its chemical complexity: Brain tissue scatters most wavelengths of light currently used to perform biological imaging, and neuronal tissue has an abundance of biomolecules that are chemically or structurally similar to the neurotransmitters we wish to detect. Furthermore, neurologically relevant processes occur at technically challenging size (nano) and time (millisecond) scales. Current tools to detect neurotransmitters have shortcomings in five broad areas that are addressed by our technology. (i) electrochemical-based tools don't have the selectivity to differentiate between molecules of similar redox potentials, (ii) electrochemical-based tools don't have appreciable spatial resolution (limited to millimeters), (iii) electrochemical tools can scar tissue limiting use, (iv) fluorescence-based tools don't have appreciable ability to report changes in extracellular concentration, and (v) and fluorescence based tools can photobleach, and may have limited use (due to load re-load requirements in case of fluorescent false neurotransmitters). Relevant literature: Kruss et al., J. Am. Chem. Soc. 2014, 136, 713-724; Tu et al. Nature 460, 250-253 (9 Jul. 2009)

SUMMARY OF THE INVENTION

We disclose an optical molecular recognition platform that utilizes polymer conjugated carbon nanotubes for the detection of neurotransmitters for use in biological samples in vitro and in vivo, including a physiological fluid like saliva or cerebral spinal fluid, as well as brain tissue, including intact brain and brain portions, such as slices. We disclose the use of polymer-functionalized carbon nanotubes for in vivo molecular detection of neurotransmitter analytes, and we exemplify our invention using the detection of neurotransmitters in a live slice of brain tissue. Our invention uses the optical properties of polymer-functionalized carbon nanotubes to detect the analyte. Detection of neurotransmitters is accomplished both in space and time, reversibly. Our sensors are biocompatiable and neurocompatible, and allow optical imaging of neurotransmitter spatial distribution, concentration, and dynamics in real time and in living tissue. The invention takes advantage of favorable fluorescence properties of carbon nanotubes, such as carbon nanotube emission in the near infrared (a region of relative optical tissue transparency), and non-photobleaching fluorescence. The near infrared emission is minimally scattered in biological systems, enabling their use in deep tissues. The non-photobleaching fluorescence of our neurotransmitter sensors enable their use in hours-long experiments. Infrared emission and non-photobleaching fluorescence benefits are features that are lacking in modern fluorescence imaging methods.

In embodiments, the invention provides;
measurement of neurotransmitter levels or dynamics in neurotransmitter concentrations using optical imaging in tissue or fluid; these measurements may be performed in the brain or peripheral nervous system of anesthetized or awake animal subjects, or in reduced brain preparations (e.g. brain slices of any species);
dynamic spatial and temporal readout of neurotransmitter concentrations in any part of the brain or peripheral nervous system. It may also be applied to measure and image neurotransmitter concentrations in tissue or fluid samples that may contain neurotransmitters;
monitoring neurotransmitter levels in biological solutions or preparations; for example in saliva or cerebrospinal fluid;
brain imaging for use in various settings such as diagnostics in health care facilities, teaching, and research in academic settings;
methods and compositions to quantitatively evaluate and or validate the mechanism of action and/or efficacy of new and or established drugs or other therapeutics that target neurotransmission. Examples of such drugs include Levodopa and dopamine antagonists (e.g. Ropinirole, Pramipexole, Loxapine, Thioridazine, Thiothixene, Trifluperidol), agonists (e.g. Modafinil, Rotigotine, Dizocilpine, Ciladopa, Fenoldopam, Rotigotine, Memantine), reuptake inhibitors (e.g. Desoxypipradrol, Troparil, Benztropine, Mesocarb, Mazindol, Altropane), and releasing agents (e.g. Phenmetrazine, Mefenorex, Amfecloral, Fenproporex). Neurotransmitter measurements may be achieved in either blood, saliva, CSF, brain tissue, brain slices, and or anesthetized or awake and behaving animals;
monitoring progression of brain diseases;
methods and compositions for identifying parts of the brain that have suffered trauma (i.e. traumatic brain injury) and can be used to determine if (and to what extent) that injury site has affected its ability to undergo normal neurotransmission behavior;
methods and compositions to determine how external stimuli (perceptual, social, chemical etc.) affect neurotransmission in the brain of awake and behaving animals;
functionalized, neurocompatible single-walled carbon nanotubes (SWNT) and their use for imaging of neurotransmitters in vivo, in live animals; and/or
sensors configured to image complex neural physiology by monitoring the spatial and temporal dynamics of neurotransmitters in live brain tissue.

In an aspect the invention provides a functionalized, neurocompatible single-walled carbon nanotube (SWNT) comprising an adsorbed neurotransmitter analyte selective polynucleotide covalently bound to a neurocompatible polyethyleneglycol (PEG).

In embodiments:
the polynucleotide is ssDNA or ssRNA;
the polynucleotide has a periodic purine-pyrimidine pattern, or any combination of purine and pyrimidine bases;
the polynucleotide is polyGT is (GT)n, wherein n is an integer 2-500, or 3-150, or 4-30, or about 15;

the analyte is a neurotransmitter selected from a catecholamine (e.g. epinephrine (adrenaline), norepinephrine (noradrenaline), and dopamine), histamine, 5-hydroxytryptamine (serotonin), γ-aminobutyric acid (GABA), glutamine, glutamic acid or a neurotransmitter metabolite selected from L-3,4-dihydroxyphenylalanine (L-dopa), 3,4-Dihydroxyphenylacetic acid (DOPAC), homovannilic acid and tyramine; and/or the PEG is PEG MW 200-40000, or 400-20000, or about 5000.

In another aspect the invention provides a functionalized, neurocompatible single-walled carbon nanotube (SWNT) comprising an adsorbed dopamine-selective polynucleotide of sequence $(GT)_6$.

In embodiments:
the polynucleotide is covalently bound to a neurocompatible polyethyleneglycol (PEG); and/or
the PEG is PEG MW 200-40000, or 400-20000, or about 5000.

The invention also provides methods of imaging neurotransmitters in vivo using functionalized, neurocompatible nanotube sensors, particularly wherein the sensors are delivered to the brain of a live mammal, such as wherein the changes in extracellular neurotransmitter concentration are detected in neural tissue, cerebrospinal fluid, blood or saliva, and particularly wherein the changes are detected in neural tissue.

The invention encompasses all combination of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

We disclose an optical molecular recognition platform that utilizes polymer conjugated carbon nanotubes for the detection of neurotransmitters for use in vivo. When a polymer is non-covalently conjugated to the surface of a single-walled carbon nanotube (SWCNT), a corona phase forms with unique molecular recognition sites for specific biomolecules (in this case, neurotransmitters). When an analyte binds to the polymer-nanotube conjugate, the corona phase is perturbed, changing the optical properties of the nanoparticle. This modulation in the fluorescent emission of the nanoparticle is reversible, and serves as the recognition signal for the analyte. This fluorescence modulation, when measured using fluorescence microscopy, provides a readout of neurotransmitter concentration with spatial and temporal resolution for in vivo experiments. Our method holds distinct advantages over other optical methods because of the near infrared emissivity of carbon nanotubes where scattering by biological tissue is minimal.

Adding to the advantages of our platform is the optical stability of carbon nanotubes that allow extended imaging with no loss of fluorescence output, a property critical for performing long-term imaging experiments that have yet to be implemented with other fluorescent probes. Our sensors convey information on neurotransmitter concentration on size and time scales that few other tools in neuroscience provide. The selectivity of the sensors for a particular neurotransmitter ensures that the signal transduced is that of a particular neurotransmitter. Some of the general utilities for our invention are:

Detection of neurotransmitter release in viable neural tissue (in vivo);

Conveying neurotransmitter concentration information on spatial and temporal scales appropriate to study physiological processes in live brain tissue;

Probing complex neural circuitry by monitoring changes in neurotransmitter concentration in different parts of the brain in real time;

Probing how neural plasticity is affected (or affects) neurotransmitter release;

Examining effect of pharmaceutical drugs on brain function as conveyed by changes in neurotransmitter concentration;

Monitoring changes in neurotransmitter concentration during behavior studies involving awake and behaving animals;

Monitoring changes in physiology (function) caused by pharmaceutical agents, brain disorders or traumatic injuries; and/or Imaging brain activity for diagnostic or therapeutic purposes.

Our SWCNT nanosensors are neurocompatible, emit in the near-infrared spectrum and offer a new optical method for detection of neurotransmitters. The optical methods enable greater spatial resolution and chronic recording. In combination with other imaging methods can provide a wealth of new information about release and diffusion, the action of drugs with abuse potential or therapeutic application.

Our invention enables non-invasively imaging dynamic neuronal activity across large swaths of the brain, making it uniquely suited to enabling neurotransmitter imaging in real-time in awake and behaving animals; for example, the invention may be used to validate drugs (antipsychotics, antidepressants, stimulants, etc) that target neurotransmission. The invention provides imaging brain circuitry on spatiotemporal scales appropriate for neuroscience and for drug validation.

Competing methods include (1) Fast scan cyclic voltometry and amperometry (FSCV), (2) CNiFERs, and (3) fluorescent false neurotransmitters (FFNs). FSCV and amperometry are electrode-based methods that use oxidation of catecholamines at a carbon fiber to report catecholamine levels. CNiFER is cell-based and is based on slow G protein-coupled receptor responses. FSCV and CNiFER methods have low spatial resolution and recording sites are placed blind to axon site. These methods have not been sufficient to enable continuous and spatially and temporally-relevant measurements of dopamine and other modulatory neurotransmitters in the neocortex. Fluorescent false neurotransmitters (FFNs) can be used to study dopamine release but are not easily loaded and reloaded for long term use. FNs do not report neurotransmitter levels in extracellular space. Calcium imaging can show bouton activity preceding release but may not report longer term release and do not report neurotransmitter levels in extra cellular space.

Advantages of our sensors in contrast to FSCV include: Cyclic voltammetry provides little in the way of spatial resolution of analytes it measures. Cyclic voltammetry probes measure millimeters at best, and must be inserted directly into brain tissue to acquire a reading. Positioning next to release sites is not feasible when they are sparse. In contrast, our nanosensors are nanometers in size (1×200 nm) and can be injected directly into brain tissue in a relatively non-invasive manner Compatible imaging methods can be used to determine distance from release sites and enables detection with high spatial resolution for comparing brain regions or for following diffusion from a site. The nanometer-scale size of our sensors enables us to report on nanometer-scale spatial changes in neurotransmitter concentration, which is relevant to the size of the synaptic cleft (300±150 nm) in which neurotransmission occurs between neuronal cells. (ii) FSCV has low selectivity for a neurotransmitter target of interest: if analytes with similar redox potentials exist within the region of interest, this signal will confound the signal from dopamine release. Cyclic voltammetry readings will report on the presence of any molecules with a similar redox potential to the target neurotransmitter. In contrast, our nanosensors are selective for a neurotransmitter of interest. (iii) Cost and user-friendliness. Compared to our nanosensors, FSCV is expensive, requires high degree of expertise to operate, and is invasive. (iv) FSCV and comparable methods are susceptible to probe fouling, such that each subsequent reading may exhibit hysteresis that is a function of electrode fouling. In contrast, our sensors have a nanosecond residence time on the nanosensors surface (as determined by molecular dynamics simulations), suggesting that there is no fouling of our sensors by chelation of biomolecules on the sensor surface. Our data show several iterations of dopamine detection in an acute brain tissue slice, exemplifying the non-fouling nature of our sensors.

Advantages of our sensors in contrast to fluorescence based techniques include (i) infinite fluorescence lifetimes (no photobleaching) enabling—for the first time—measurement of neurotransmitters for hours-long timescales in artificial cerebrospinal fluid (aCSF). (ii) Our nanosensors are reversible. CNiFER can only report on the cumulative GPCR activity. FFNs only report on neurotransmitter release. Our sensors can directly report both the appearance but also the disappearance of neurotransmitters in extracellular space. This enables us to measure both neurotransmitter release and neurotransmitter re-uptake, both of which are key elements of modulatory neurotransmission. In areas of sparse release, we may also be able to visualize diffusion from a release site, which would also add new ability. (iii) Our nanosensors are nano-scale. CNiFER are the size of HEK293 cells that encode their signal (10-15 µm). Therefore, CNiFER are inherently more 'invasive' when inserted into brain tissue, as they require a larger accommodation volume. Additionally, CNiFER can only report on indirect GPCR activity within a spatial limit of detection that matches their size (tens of microns). Conversely, our sensors are nanometers in size (1 nm×200 nm) and can be used to report on nanometer-scale spatial changes in neurotransmitter concentration, which is relevant to the size of the synaptic cleft (300±150 nm) in which neurotransmission occurs between neuronal cells. (iv) CNiFER cells respond on the timescale of seconds to minutes, whereas our sensors respond on millisecond timescales. In other words, from the time when a neurotransmitter is released until the sensor responds to its presence, CNiFER cells will have a second to minute-long time lag. Our sensor's millisecond temporal responsivity matches the time-scale upon which neurotransmitters are released in the brain. (v) Our sensor signals can penetrate tissue and bone with a near-infrared signal. Unlike other fluorescent methods, we can acquire fluorescence signal with less scatter from our sensor through brain tissue and through bone (cranium) tissue. We demonstrate the bone-penetrating capabilities, in which we have placed our sensors on top of a mouse cranium, and monitor the fluorescence of these nanosensors upon addition of neurotransmitter. We can detect a clear increase in fluorescence upon addition of neurotransmitter through the mouse cranium.

A significant utility of our invention lies in its ability to help probe complex neural physiology by monitoring the spatial and temporal dynamics of neurotransmitters in live brain tissue; for example, the effects of pharmaceutical therapies on brain function can be studied in real time.

In an aspect the invention provides a functionalized, neurocompatible single-walled carbon nanotube (SWNT) comprising an adsorbed neurotransmitter analyte selective polynucleotide covalently bound to a neurocompatible polyethyleneglycol (PEG).

SWNTs comprising an adsorbed neurotransmitter analyte selective polynucleotide are known in the art, and the methods of making and criteria for selecting analyte selective polynucleotides are established. Suitable polynucleotide are typically, ssDNA or ssRNA, which may be present in a variety of structural conformations. Preferred polynucleotides have a periodic purine-pyrimidine pattern, such as polyGT is (GT)n, wherein n is an integer, such as 2-500, or 3-150, or 4-30, or in a particular example, about 15.

We have validated the disclosed methods with a variety of neurotransmitter analytes, including catecholamines, histamine, 5-hydroxytryptamine (serotonin), γ-aminobutyric acid (GABA), glutamine, glutamic acid, L-3,4-dihydroxyphenylalanine (L-dopa), 3,4-Dihydroxyphenylacetic acid (DOPAC), homovannilic acid and tyramine.

Suitable neurocompatible polyethyleneglycol (PEG) components are readily determined empirically, confirmed by lack of effective toxicity, as exemplified below, and include a variety of structures (e.g. branching) and molecular weight, including PEG MW 200-40000, or 400-20000, or about 5000.

To demonstrate our nanosensor's utility in living brain tissue, we detail experiments herein in which the release of endogenous neurotransmitter is monitored from acute brain slices stimulated by high potassium ($K^+$) containing buffer solution. We describe the synthesis of the sensors, detail the preparation of brain slices embedded with our neurotransmittersensors, and provide experimental details for the imaging of brain slices embedded with our nanosensors.

EXAMPLES

1. Imaging Dopamine in Brain Tissue Using Synthetic Infrared Nanosensors

The optical nanosensors are synthesized by suspending single walled carbon nanotubes in pegylated $(GT)_{15}$ DNA by probe tip sonication in a 100 mM NaCl buffer solution. The pegylation of the DNA strand can be achieved by reacting maleimide end-modified polyethylene glycol (PEG, 3 kDa) with a 5' thiolated $(GT)_{15}$ DNA. The pegylated DNA is then sonicated for 10 minutes at ~5 W power setting. Finally, the sonicated mixture is centrifuged to remove unsuspended nanotubes, and the recovered supernatant characterized using a UV-Vis spectrometer. This simple and easily scalable process gives a stable sensor suspension that can be stored at room temperature for extended time periods. The user can dilute the suspensions to desired nanotube concentrations for in vivo and in vitro use.

Acute brain slices are prepared from anesthetized mice. The brain is quickly extracted from the skull and mounted on a vibratome for slicing. The vibratome was pre-chilled to 4° C. and the sample tray filled with $O_2$ saturated aCSF buffer. At all times, the brain and recovered brain slices were kept in continuously gassed (95% $O_2$, 5% $CO_2$) aCSF buffer at 4° C. Sensors were diluted to a nanotube concentration of 25 mg/L in PBS (phosphate buffered saline) before being injected into the brain. Approximately 20 μL, of sensor volume was injected into the mounted brain using Hamilton Neuros Syringes, from which 300 μm slices were recovered. After recovery of 3 such slices, an additional 20 μL of sensor was injected into the brain, after which brain slices continued to be recovered. 20 μL sensor volume was injected for every 3 slices recovered from the brain until enough brain slices were recovered for the experiment. Each 20 μL volume injection was delivered into three to five distinct regions to enable neurotransmitter detection in various regions of the brain.

Sensors are delivered into the brain via injection. The injection site and its periphery will house a bolus of sensors, which detect neurotransmitter molecules and changes in neurotransmitter concentration as neurotransmitter diffuses out of their point of release. Owing to their small size, some of our sensors may be inside the synaptic region (interface between two neuronal axons where neurotransmitter release takes place); however, a significant portion of the injected sensors will be extrasynaptic in location. Regardless of their location, diffusion of neurotransmitters is the primary mechanism by which neurotransmitters signal between cells. Once in contact with extracellular sensors, neurotransmitter molecules (or other specific sensor analytes) cause conformational changes of the pegylated $(GT)_{15}$ DNA on the surface of the nanotube, resulting in modulation of fluorescence behavior; in the case of neurotransmitter detection, the modulation produces a rapid increase in the fluorescence of the carbon nanotubes.

The depolarization wave that triggers release of neurotransmitter can be elicited using electrical, chemical, or optical stimulation. For our demonstration, we use chemical stimulation using a high 15-35 mM potassium ($K^+$) aCSF buffer. The high concentration of potassium causes an ion imbalance between the cytoplasmic and extracellular environment, which causes neuronal membrane depolarization and neurotransmiter release.

We imaged direct nanosensor-based neurotransmitter release in brain tissue in four acute slices, and representative intensity-time traces. When neurotransmitter is released from neurons, the near-infrared fluorescence intensity of our sensors increases. The increase in intensity is normalized and presented as a plot against time in four different brain slices. Our results show the near-infrared fluorescence spectra of our sensors, and the characteristic multi-peak emission of our sensor emission profile. This spectrum serves to confirm that the sensor intensity increase imaged in the brain tissue slice is caused by modulations in the fluorescent properties of the nanotubes (as a result of neurotransmitter release), and not an artifact caused by changes in baseline tissue fluorescence.

We also tested the reversibility of our sensors in living neural tissue. Reversibility demonstrates that once neurotransmitter causes conformational changes that increase fluorescence intensity of our sensors, the subsequent removal of neurotransmitter from the extracellular space can reverse the fluorescence intensity increase, in effect resetting our sensors for detection of subsequent neurotransmitter release events. Sensor reversibility is vital to monitoring dynamic neurotransmitter concentrations, and a feature lacking in many existing technologies for neurotransmitter detection.

We have confirmed our neurotransmitter nanosensor is functional in ex vivo striatal tissue by using high K+ to drive bulk neurotransmitter release, for multiple stimulation and wash cycles, over the course of 80 minutes. These data also reduce concerns about potential "biofouling" in which the sensor is activated or inactivated by non-specific binding when placed in tissue, or in which the sensor degrades after repeated use or after extended time.

In vitro experiments show the neurotransmitter nanosensors can report neurotransmitter concentrations that range from 100 nM to 0.1 mM, a range relevant to endogenous neurophysiology. At the single sensor level, we can detect picomolar (pM) quantities of neurotransmitter. The through-cranium neurotransmitter detection capabilities we demonstrate, enabled by the tissue and bone-transparency of infrared fluorescence wavelengths emitted by our sensors, indicate our sensors will enable detection of neurotransmitters in an intact brain structure, through the cranium bone.

We have applied our model of sensor response in striatal tissue to the expected pattern of neurotransmitter release as detailed in the literature, for both positive and negative reward prediction error responses. We estimate that neurotransmitter release driven by a shift from tonic firing at 5 Hz to a phasic burst at 20 Hz for 500 msec (a positive reward prediction error) should be induce a deltaF/F of 0.27 using bulk phase detection. Movement from a tonic rate at 5 Hz to 1 Hz pause for 500 msec (a negative reward prediction error) should produce a delta F/F of −0.07. These delta F/F estimates are modest but sufficient and are comparable to levels reported in experiments using genetically encoded calcium indicators such as GCAMP for functional imaging in rodents. These estimates indicate that this sensor is a useful tool for detection of changes in modulatory neurotransmitter levels relevant to behavioral studies in awake behaving animals.

We have tested and confirmed imaging of a panel of neurotransmitter analytes, including epinephrine (adrenaline), norepinephrine (noradrenaline), dopamine, 5-hydroxytryptamine (serotonin), glutamic acid, L-3,4-dihydroxyphenylalanine (L-dopa), 3,4-Dihydroxyphenylacetic acid (DOPAC), homovannilic acid and tyramine 2. Molecular Recognition Mechanisms Revealed in DNA-Wrapped Carbon Nanotubes In this example we demonstrate molecular recognition mechanisms underlying the SWNT sensing activity. Varying the length of DNA polymers wrapping SWNTs yielded highly selective sensors for molecular analytes dopamine and norepinephrine. Molecular dynamics studies identified that the selectivity in these new sensors originates from DNA polymers that assume circular conformations on SWNTs, and perfectly wrap the SWNT once along its circumference. We identify that DNA conformations create distinct modulations of the electrostatic environment within SWNT, which can lead to enhanced localization of the exciton. We also observe charge transfer to SWNTs in ssDNA-SWNT composites, which can influence exciton relaxation pathway and relaxation rates. Surfactant exchange reveals dopamine molecular recognition mechanism: polynucleotide surface coverage.

To identify the mechanisms that enable selective molecular recognition of dopamine by SWNT-based optical nanosensors, we performed all-atom molecular dynamics (MD) simulations, quantum mechanical (QM) calculations, and fluorescence imaging of the $(GT)_{15}$-SWNT nanosensor selective for neurotransmitter dopamine. MD simulations reveal that polymer length dictates the structure of the polymer on the SWNT, whereby 12 nucleoside-length single-stranded DNA (ssDNA) polymers form rings around SWNT instead of helices. The SWNT surface-adsorbed polymer generates patterns of electrostatic potentials on the SWNT surface and strongly localizes excitons, leading to a prevalence of non-radiative exciton recombination in SWNT. MD and QM calculations identify charge transfer between the polymer wrapping and the SWNT as the mechanism of PL attenuation, which can be reversed in the presence of the neurotransmitter analyte. Quantum mechanical (QM) calculations show that adsorbed nucleosides of the polymer dope the SWNT, forming charge transfer sites along the nanotube axis. In the presence of these doping sites, strongly localized excitons recombine efficiently through a dominant non-radiative multiphonon decay process. This decay is abolished or severely slowed in the presence of dopamine, leading to the brightening of photoluminescence (PL). We validate our calculations with fluorescence spectroscopy and microscopy of SWNT nanosensors, and demonstrate that we can implement our QM and MD strategy to control exciton recombination and analyte selectivity to discover a new fluorescent sensor for neurotransmitter norepinephrine. Our work explores the wide range of time-scales over which fluorescent probes selectively photoluminesce in the presence of neurological targets: charge transfer (femtosecond via QM calculations), selective analyte binding and exciton recombination (nanosecond via MD simulations), and neurotransmitter imaging (millisecond via infrared microscopy).

MD simulations show DNA polymer length modulates helix-to-ring transition on SWNT. Variations in the fluorescence (the PL quantum yield) of SWNTs wrapped by different polymers can depend on the chemical composition of the polymers, interaction types and strengths, and the physical parameters of the SWNT environment, such as the dielectric screening. We implement MD simulations of known SWNT-based dopamine nanosensor $(GT)_{15}$-SWNT to elucidate how the polymer creates patterns in the electrostatic environment of the SWNTs, and to examine how this environment affects SWNT PL. The initial states of ssDNA-SWNT systems were based on reported structures of ssDNA adsorbed to SWNT, which demonstrated that ssDNA polymers wrap SWNTs helically. Our MD simulations show that $(GT)_{15}$ ssDNA remains equilibrated onto the SWNT surface in a helical structure within the 200 ns simulation length, consistent with previous studies, and showed no significant structural deviations from its initial helical conformation.

To examine the electrostatic effect of the ss-$(GT)_{15}$ polymer on SWNT, we calculated the electrostatic potential induced by the ss-$(GT)_{15}$ at the SWNT surface. The calculated potential includes all molecules present in the SWNT environment: the ssDNA polymer, water, and ions, including the $Na^+$ cations adsorbed over long timescales within DNA pockets. We find that ss-$(GT)_{15}$ induces regions of negative and positive electrostatic potential as a 'footprint' under the polymer, which extend ~4 nm in contiguous length, and roughly follow the helical pattern of the ssDNA.

Motivated by the observed electrostatic footprinting of polymers adsorbed to SWNT, we further explored alternate $(GT)_n$ ssDNA polymer-SWNT structures, where n indicates ssDNA polymers containing a varying number of repeating (GT) units. While ssDNA molecules that encapsulate SWNTs several times are observed to adopt helical conformations, shorter ssDNA oligonucleotides adopt different surface adsorbed patterns, which can afford a unique control parameter over electrostatic footprinting and SWNT exciton recombination. In particular, SWNTs that are widely used for fluorescence imaging and sensing have ~1.2 nm diameters, which can accommodate a singly wrapped 12-mer (4.08 nm long) oligonucleotide. Thus, we performed MD simulations of $(GT)_6$ oligonucleotide initially helically equilibrated to the surface of a (9,4) SWNT, to replicate the initial conditions of the simulated $(GT)_{15}$-SWNT system. During a short 20 ns simulation, $(GT)_6$ polymer rearranged from its initial helical conformation to a ring-like structure; such helix-to-ring transitions were reproducibly observed in >5 independent MD simulations. While the system contains a single ssDNA molecule, fluorescent SWNT nanosensors typically contain many ssDNA molecules adsorbed onto a single SWNT. Therefore, to better emulate experimental conditions, we examined multiple ssDNA-$(GT)_6$ polymers wrapping the SWNT. Following simulation, we again observe helix-to-ring transition for all $(GT)_6$ polymers. The DNAs in ring conformations are highly ordered, as evidenced by distinct sharp peaks that appear at approximately equal intervals in the radial distribution function of DNA phosphate groups. Electrostatic footprinting induced by the ring-like structures of $(GT)_6$ polymers on SWNT is observed, following the physical adsorption pattern of the electrostatic potential induced by the $(GT)_6$ polymer. The resulting electrostatic potential map on the SWNT surface appears in distinct ring-like regions of alternating positive and negative potential along the SWNT surface, where each electrostatic pocket measures ~1.5 nm in contiguous length. The negative electrostatic potential pockets are observed primarily beneath guanine nucleotides, while the positive electrostatic potential pockets are observed beneath thymine nucleotides.

Electrostatic footprinting of SWNT by circumference-length $(GT)_N$ polymers yield high turn-on sensors for dopamine and norepinephrine. For in vivo applications of neurotransmitter nanosensors, a strong fluorescence turn-on response is necessary. Prior work shows that the fluorescence intensity of ss$(GT)_{15}$-SWNT increases by as much as 90% upon exposure to 100 µM dopamine. At physiological concentrations (~1 µM), the expected ΔF/F is on the order of 30%. Dopamine addition to the ss$(GT)_{15}$-SWNT sensor does not perturb the SWNT absorption cross section, thus the fluorescence intensity increase results from an increase in dopamine-induced SWNT quantum efficiency. Guided by the theoretically predicted electrostatic confinement of SWNT excitons by $(GT)_6$ polymers, we synthesized a $(GT)_N$ based ssDNA polymer library to probe the effects of polymer conformation on nanosensor sensitivity and selectivity to neurotransmitter dopamine We produced a library of $(GT)_N$ ssDNA sequences for N=1, 4, 6, 7, 8, 12, 15, 19, 22, 26, and 30 using a previously-described protocol. All sequences from N=4 to N=30 produced DNA-SWNT suspensions, with the exception of N=1 that did not suspend SWNT. We measured each $(GT)_N$-SWNT sensor's response to 100 µM dopamine Consistent with previous results, dopamine addition increases SWNT fluorescence for all sequences. We observe a surprising length-dependent trend in nanosensor response to 100 µM dopamine, for which the previously reported $(GT)_{15}$-SWNT nanosensor represents an apparent minimum ($\Delta F/F_0$=45%), and $(GT)_6$-SWNT a maximum ($\Delta F/F_0$=3500%). Short $(GT)_N$ repeats (N=4, 6, 7, 8) yield $\Delta F/F_0$=1400%, 2400%, 1700%, and 1000% in response to 100 µM dopamine, respectively, for the (9,4) SWNT chirality. For longer sequences (N=12, 15, 19, 22, 26, 30), we observe corresponding $\Delta F/F_0$=45%, 45%, 50%, 60%, 40%, and 150% in response to 100 µM dopamine, respectively. We identify ssDNA polymers capable of ring-like electrostatic footprinting as having strong turn-on responses to dopamine.

We next examined the baseline fluorescence intensity of equimolar aliquots of each DNA-SWNT suspension in our library, we observe that short (GT) repeat sequences (N=4, 6, 7, 8) exhibit strongly quenched baseline fluorescence, representing 25%, 5%, 15%, and 40% of the baseline fluorescence exhibited by $(GT)_{15}$-SWNT when compared at the (9,4) chirality peak. Conversely, long sequences (N>=12) exhibit approximately the same degree of baseline fluorescence as compared to $(GT)_{15}$-SWNT. In general, the pre-dopamine fluorescence of $(GT)_N$-SWNT suspensions is lower for sequences where N≤8, indicating that polynucleotide sequences exceeding roughly twice the average SWNT circumference in length will adopt a helical SWNT-adsorbed structure, as confirmed by our MD simulations of $(GT)_{15}$-SWNT and $(GT)_6$-SWNT. We thus identify polymer length as a key modulator of SWNT fluorescence quantum yield, which can be exploited for maximizing nanosensor $\Delta F/F_0$ signal. We further identify the $(GT)_6$-SWNT complex as the most suitable nanosensor for imaging dopamine and norepinephrine. DNA-SWNT absorption spectra remain invariant to the addition of dopamine, further indicating that quantum yield increases are what drive the increase in fluorescence for short and long sequences.

To validate the potential in vivo imaging use of $(GT)_6$ SWNT for dopamine and norepinephrine, we developed fluorescence response curves for $(GT)_6$-SWNT suspension by varying concentrations of norepinephrine and dopamine We fit our experimental data using the Hill equation to obtain the dissociation constant for sensor-analyte interaction. We determined the dissociation constants to be 15 µM for norepinephrine and 20 µM for dopamine. Both dopamine and norepinephrine fluorescence turn-on behavior is suitable for measuring neurotransmitter concentrations in biologically-relevant regimes encompassing tonic and phasic firing indicating these sensors are suitable for in vivo imaging of modulatory neurotransmission. A burst of activity from dopaminergic neurons in the striatum can yield local dopamine concentrations on the order of 1 µM to 5 µM. The strong turn-on response of $ss(GT)_6$-SWNT nanosensors is crucial for studying the slow tonic firing of dopaminergic neurons where extracellular dopamine concentrations vary transiently from 10 nM to 100 nM. Under such neuronal activity, only $(GT)_6$-SWNT sensors produce a strong $\Delta F/F_0$ signal to enable in vivo use, and discriminate between transience in tonic firing. We note that compared to the previously reported $ss(GT)_{15}$ based dopamine sensor, the dopamine-induced fluorescence response from our $ss(GT)_6$ sensor is nearly an order of magnitude higher, and significantly more selective toward dopamine and norepinephrine, showing nearly no cross-responsivity for other neurologically-relevant analytes in our screening library. We owe this increased selectivity to the molecular modes of interaction between the catecholamine and nucleosides on the DNA polymer of $ss(GT)_6$-SWNT, as we describe below. Control experiments with $(C)_{30}$-SWNT and $(C)_{12}$-SWNT show these DNA-SWNT conjugates are non-responsive when exposed to either dopamine or norepinephrine, attributing the selectivity of our nanosensors to the (GT) base sequence, and the sensitivity to the polymer length and subsequent SWNT electrostatic footprinting.

Polymer length modulates stability of polymer on SWNT. We examined the stability of all $(GT)_N$-SWNT suspensions using fluorescence and absorbance spectroscopy. To rule out the possibility that spontaneous DNA polymer rearrangement contributes to the large increase in nanosensor fluorescence after addition of dopamine, we measured the time-dependent fluorescence of all $(GT)_N$-SWNT suspensions using fluorescence spectroscopy. Prior work shows that DNA-SWNT fluorescence stability directly correlates with DNA polymer stability on the SWNT. To test stability using fluorescence, we diluted all $(GT)_N$-SWNT suspensions to equimolar SWNT concentrations and measured their fluorescence spectra over the course of 140 minutes immediately following dilution. Most of the $(GT)_N$-SWCNT suspensions we examined exhibited stable fluorescence (<–15% change) with the exception of $(GT)_4$-SWNT, which showed a final –40% modulation in fluorescence. For all $(GT)_N$-SWNT suspensions, the time-dependent fluorescence modulations were negative, compared to the increase in fluorescence induced by dopamine, further confirming that increase in fluorescence observed immediately after addition of dopamine is due to the dopamine analyte, and unlikely to have been caused by volume perturbations or spontaneous polymer rearrangement on the surface of the carbon nanotube. The differences in fluorescence modulation experienced by each suspension indicate that polymer length affects the base stacking stability of the $(GT)_N$-SWNT suspensions with an apparent instability for N≤4. Absorbance measurements support the trend observed from fluorescence measurements. Absorbance measurement of the as-made $(GT)_N$-SWNT suspension exhibits strong absorption at ~260 nm, suggesting excess, unadsorbed DNA in solution. The absorbance peak at 260 nm is abolished by removing unsuspended polymer by filter centrifugation. Absorbance measurements at the DNA absorbance peak reveal that no ssDNA polymer desorption occurs from any $(GT)_N$-SWNT sample, with the exception of $(GT)_4$-SWNT that shows appreciable $(GT)_4$ polymer desorption from SWNT after one week at room temperature. Our results indicate that $(GT)_N$ sequences with N>4 form stable non-covalent conjugates with SWNT and that SWNT PL modulation observed in the presence of dopamine results from the polymer-mediated modulation in SWNT quantum yield.

Surfactant exchange reveals dopamine molecular recognition mechanism: dopamine-binding pockets from polymer surface coverage. We measured the relative surface coverage of SWNT by $(GT)_N$ polymers in our library with surfactant exchange experiments. When added ssDNA-SWNT, surfactant sodium cholate (SC) adsorbs to exposed SWNT surface, and can also displace weakly adsorbed DNA regions, causing a solvatochromic SWNT fluorescence peak shift, as reported previously. Addition of 1 wt % SC to $(GT)_N$-SWNT induces solvatochromic shifts in SWNT fluorescence peaks, with the largest solvatochromic observed for $(GT)_4$-SWNT, further indicating $(GT)_4$ is the least stably adsorbed sequence on the SWNT. Sequences above N=4 (N=6 to N=30) all showed minimal SC-induced solvatochromic shifting, indicating that for polymer lengths >4, polynucleotide polymers remain stably bound to the SWNT. We repeated SC solvatochromic shift experiments for all $(GT)_N$-SWNT suspensions pre-incubated in 100 µM dopamine Surprisingly, addition of dopamine to $(GT)_N$-SWNT suspensions pre-incubated with dopamine either reduces or eliminates the SC-induced solvatochromic shifting. As such, it appears that dopamine stabilizes polymer adsorption onto the SWNT surface, even for polymers such as N=4 previously identified to be unstably bound. We disclose that dopamine stabilization of $(GT)_N$ polymers on SWNT arises from a selective interaction between dopamine and $(GT)_N$-SWNT, and further, that dopamine trapped in these $(GT)_N$ polymer binding pockets enhance PL by direct interaction with the adsorbed polymer and the SWNT, and as a result of these interactions, the PL quantum yield of SWNT sensors is selectively enhanced by polymer-induced trapping of dopamine.

Adsorbed Dopamine Modulates ssDNA Conformation and Electrostatic Potential at SWNT. To further examine the molecular recognition mechanism of dopamine by $(GT)_N$-SWNT nanosensors, we performed all-atom MD simulations of ssDNA-$(GT)_{15}$ and ssDNA-$(GT)_6$-SWNT in the presence of dopamine. Several independent MD simulations revealed that dopamine can influence ssDNA conformations and that dopamine has multiple binding poses that are transient.

We prepared representative binding poses of dopamine to ssDNA-$(GT)_{15}$ and ssDNA-$(GT)_6$-SWNTs. Dopamine can insert into SWNT regions that transiently have no DNA coverage, and be stabilized by simultaneously stacking to the SWNT and hydrogen bonding to neighboring DNAs nucleotides. Also, dopamine can bind to ssDNA-$(GT)_{15}$-SWNT so that it raises neighboring DNA bases. Occasionally, when dopamine stacks on SWNT, DNA nucleotides can also cover dopamine and form stacked sandwich-like structures. The bound dopamine contributes to the potential created at the SWNT surface. Our poses show the electrostatic potential beneath dopamine for several representative binding poses on the SWNT surface. Dopamine binding usually corresponds to extension of the electrostatic potential regions. Such modulations in the potential are likely to affect exciton localization.

Two different mechanisms of binding of dopamine to longer and shorter ssDNA wrapping SWNT are indicated. In the case of ssDNA-$(GT)_{15}$, dopamine is trapped between two ssDNA pitches close to the end of ssDNA-$(GT)_{15}$ where two raised thymine bases trap dopamine. However, the mechanism of dopamine adsorption to ssDNA-$(GT)_6$-SWCNT is different; here, dopamine binds between two successive ssDNA-$(GT)_6$'s. The adsorbed dopamine extends the positive and negative potential domains and leads to exciton size extension. Opened water windows by adsorbed dopamine between two ssDNA-$(GT)_6$'s enhances the extension of electrostatic potential pattern leading to less exciton localization at the SWNT surface and brighter PL response of ssDNA-$(GT)_6$-SWCNT conjugates.

Polymer surface density determines density of dopamine binding sites. Our results thus far demonstrate that the conformation of surface-adsorbed ssDNA polymers on SWNT influences SWNT fluorescence and enables tuning of nanosensor responses by affording control over the DNA-SWNT baseline fluorescence. Based on our molecular dynamics and experimental results, we hypothesized that tuning the surface density of $(GT)_6$ on the SWNT surface will affect the resulting SWNT electrostatic footprint, and thus enable more precise control of the baseline fluorescence of the DNA-SWNT conjugate. We therefore varied polymer surface packing by synthesizing DNA-SWNT conjugates with different mass proportions of SWNT (mS) and ss(GT)$_6$-DNA (mD). The resulting DNA-SWNT conjugates thus had variable surface-adsorbed polymer density. We prepared three suspensions at mS/mD mass ratios of 2, 5 and 10. The resulting fluorescence intensity from equimolar SWNT aliquots shows a clear trend whereby higher polymer surface densities (mS/mD=2) exhibit the strongest fluorescence quenching. Addition of 10 µM of dopamine enhances the SWNT fluorescence of all three samples; however, the nanosensor response is highest for the SWNT sample (mS/mD=2) that is most strongly pre-quenched prior to dopamine addition. These results reveal that (i) the degree of fluorescence quenching of SWNT by adsorbed DNA is a function not only of polymer conformation (ring vs. helix) but also of the polymer surface density; the greater the surface coverage, the stronger the SWNT PL quenching; (ii) the higher the surface coverage, the higher the number of dopamine binding pockets; and (iii) dopamine enhances quantum yield in proportion to the number of available binding sites.

References

1. Manohar, S., T. Tang, and A. Jagota, Structure of homopolymer DNA-CNT hybrids. The Journal of Physical Chemistry C, 2007. 111(48): p. 17835-17845.
2. Yang, M., V. Koutsos, and M. Zaiser, Interactions between polymers and carbon nanotubes: a molecular dynamics study. The Journal of Physical Chemistry B, 2005. 109 (20): p. 10009-10014.
3. Johnson, R. R., A.T.C. Johnson, and M. L. Klein, Probing the structure of DNA-carbon nanotube hybrids with molecular dynamics Nano Letters, 2008. 8(1): p. 69-75.
4. Kruss, S., et al., Neurotransmitter detection using corona phase molecular recognition on fluorescent single-walled carbon nanotube sensors. Journal of the American Chemical Society, 2014. 136(2): p. 713-724.
5. Beyene, A. G., G. S. Demirer, and M. P. Landry, Nanoparticle—Templated Molecular Recognition Platforms for Detection of Biological Analytes. Current protocols in chemical biology, 2016: p. 197-223.
6. Landry, M. P., et al., Comparative dynamics and sequence dependence of DNA and RNA binding to single walled carbon nanotubes. The Journal of Physical Chemistry C, 2015. 119(18): p. 10048-10058.
7. Kato, Y., et al., Thermodynamics on soluble carbon nanotubes: how do DNA molecules replace surfactants on carbon nanotubes? Scientific reports, 2012. 2: p. 733.
8. Schoppler, F., et al., Molar extinction coefficient of single-wall carbon nanotubes. The Journal of Physical Chemistry C, 2011. 115(30): p. 14682-14686.
9. Choi, J. H. and M. S. Strano, Solvatochromism in single-walled carbon nanotubes. Applied Physics Letters, 2007. 90(22): p. 223114.
10. Tu, X., et al., DNA sequence motifs for structure-specific recognition and separation of carbon nanotubes. Nature, 2009. 460(7252): p. 250-253.
11. Johnson, R. R., et al., Free energy landscape of a DNA-carbon nanotube hybrid using replica exchange molecular dynamics Nano letters, 2009. 9(2): p. 537-541.
12. Salem, D. P., et al., Chirality dependent corona phase molecular recognition of DNA-wrapped carbon nanotubes. Carbon, 2016. 97: p. 147-153.

3. An Optical Nanosensor for Imaging Dopamine Neuromodulation in the Extracellular Space of Striatal Tissue In this example we designed a nanoscale near-infrared fluorescent reporter for neuromodulator dopamine and demonstrate its efficacy for imaging dopamine volume transmission in the extracellular space of both the brain striatum and cortex. The nanosensor images dopamine release and reuptake dynamics in the extracellular space arising from evoked as well as spontaneous release with few-terminal spatial resolution. We show that dopamine volume transmission exhibits highly heterogeneous behavior with apparent dopamine reuptake constants that span over an order of magnitude. Inhibiting dopamine reuptake with antidepressant drug nomifensine reveals that dopamine clearance is predominantly diffusion mediated immediately following release, but dopamine transporter mediated at longer times after release. We observe spatially-correlated dopaminergic signaling dynamics, indicating brain regions of high release synchrony in the striatum. The probe reports dopamine volume transmission at spatial scales that have heretofore been inaccessible with existing investigative tools and can be employed to relate extracellular dopamine concentration dynamics with extrasynaptic receptor activation, neuronal activity, and behavior.

Herein we report a near-infrared fluorescent nanosensor for dopamine (nIRDA) that effectively records dopamine neuromodulation in mouse brain slice preparations. The sensor is synthesized by non-covalently conjugating a $(GT)_6$ polynucleotide sequence to fluorescent single wall carbon nanotubes (SWNT). The sensor provides a reversible up to 3000% $\Delta F/F$ fluorescent response upon exposure to dopamine, which is used to image transients in ECS dopamine concentration. The nanosensor provides homogenous labeling of brain tissue, which affords terminal-level spatial resolution, and sensor-analyte binding kinetics that enable video-rate recording of fluorescence modulation with high ##-ms temporal resolution. Our results demonstrate neurochemical imaging of dopamine dynamics in the striatum and cortex ECS with relevance for in vivo investigation of dopamine's critical functions in goal-directed behavior and motor control, and dysfunctions that lead to disease.

Dopamine transients in acute brain slices can be imaged using near-infrared nanosensors We designed near-infrared fluorescent dopamine sensors (nIRDAs) that report on dopamine in the extracellular space of neuronal tissue. nIRDAs are synthesized from single wall carbon nanotube (SWNT) fluorescent reporters electrostatically conjugated with synthetic polymers to build nanometer-scale probes that can selectively report on local dopamine concentration through a near-infrared change in fluorescence ($\Delta F/F$) of up to 3000% and with a dynamic range of uM to nM dopamine nIRDAs exhibit strongly quenched baseline fluorescence and yield a strong turn-on fluorescence response selectively in the presence of dopamine. Fluorescent nanosensor parameters previously determined as optimal enable nIRDAs to capture low amplitude transients in dopamine concentration arising from the activity of just a few boutons.

We chose to validate nIRDAs by imaging dopamine neuromodulation in acute striatal brain slices. The striatum is a large subcortical structure with homogenous and dense enervation by dopaminergic projections from the SNc. The striatum also receives major glutamatergic afferents from the cortex, whereas medium spiny neurons (MSN), the resident neurons of the striatum are GABAergic. Furthermore, cholinergic interneurons feature prominently in the striatum. nIRDAs exhibit strong selectivity for dopamine over competing neurotransmitter molecules GABA, glutamate, and acetylcholine. We prepared coronal mouse brain slices, which we incubated with 5 mg·L$^{-10}$f nIRDAs for 10 minutes to enable sensors to localize into the brain tissue. Slices were subsequently rinsed to remove excess or unbound nIRDAs. We found that this method afforded extensive and homogenous labeling of most parts of the coronal slice, including the dorsal striatum, where imaging of dopamine neuromodulation is performed. Furthermore, prior work confirms that SWNT-based fluorophores localize in the ECS of brain tissue.

To image neuromodulation in the striatum with nIRDAs, we evoked dopamine release using both high potassium stimulation (K-stim) and with selective optogenetic stimulation of dopaminergic terminals (L-stim), which ensures that only dopamine is released into synaptic clefts and the ECS. For L-stim, brain slices were prepared from mouse that were virally transfected to express the light sensitive ion channel, channelrhodopsin (Chr2), in dopaminergic terminals of the striatum. Upon optical stimulation with a 473 nm laser, we observe fluorescence modulation of nIRDAs embedded in striatal tissue. The fluorescence modulation is transient whereby its onset coincides with time of stimulation, and is spatially colocalized with dopaminergic boutons exhibiting high degree of Chr2 expression. When slices are labeled with SWNT-polymer constructs that are insensitive to dopamine, no modulation in fluorescence is observed upon repeated stimulation by light. Furthermore, slices that do not express Chr2 in dopaminergic terminals are insensitive to light stimulation as shown by a lack of fluorescence modulation of nIRDAs. Stimulation of wild type striatal tissue slices with high potassium ACSF buffer (15 mM-20 mM $K^+$ ions) also elicits nIRDA fluorescence transients. While light-stimulated dopamine release events in optically active slices are instantaneous and exhibit fast release and re-uptake dynamics (~2 s), stimulation by $K^+$ produces dopamine dynamics that are considerably slower (~10 s). During the course of imaging experiments, we also observe nIRDA fluorescence transients that are not elicited by stimulation but rather occur spontaneously, which we attribute to tonic dopamine release and re-uptake. These results collectively indicate that nIRDAs represent an imaging platform to probe dopamine kinetics in the brain ECS.

Spatial analysis of nIR-DAS fluorescence modulation. A key benefit of imaging neuromodulation lies in the temporally-resolved spatial information that can be garnered from imaging evoked and spontaneous dopamine release. Dopamine concentration transients in the ECS have been studied using electrochemical techniques such as FSCV. Despite the notable role FSCV has played in elucidating DA dynamics in the ECS, it is a tool that assays overflow from the ensemble activity of hundreds of dopaminergic terminals; it is not suited for capturing terminal level spatial information because of the size of the carbon fiber electrode. As a result, information about dopamine volume transmission at inter-terminal distances has remained largely inaccessible, and the information collected reports on the average behavior of hundreds of terminals, averaging heterogeneities that may be present in individual synapses. nIRDAs provide the spatial granularity required to probe terminal-scale dopaminergic activity to visualize local heterogeneities in dopamine reuptake, the temporal synchrony of release from terminal clusters, and the diffusive evolution of release from a single terminal.

In a representative recording, we analyzed the activity of seven highly active regions of interest (ROI) exhibiting spontaneous (non-evoked) dopamine release and reuptake activity. The regions examined spread over ~100 μm and exhibited synchronized dopamine activity. Correlation analysis revealed the presence of two ROI clusters with high intracluster synchrony and high intercluster asynchrony despite their spread over a 100 μm distance. Our results indicate that neurons can synchronize dopamine release over hundred-micron distances, which is surprising considering that neurotransmitter release is a highly stochastic process with low release probabilities (<10%) for dopaminergic terminals in the striatum. Equally remarkable is the strong asynchrony observed between the two clusters, which indicates the clusters belong to two distinct projection axons with overlapping striatal arborizations. This type of synchronized behavior is observed during imaging of evoked dopamine release as well.

During evoked activity imaging, nIRDA fluorescence modulations can be spatially confined, or can evolve across the imaging field of view, enabling temporal analysis of the spatial evolution of dopamine in the ECS. We present an example of light-stimulated dopamine release for which the spatial granularity afforded by nIRDAs enables tracking of dopamine fluorescence hotspots over a spatio-temporally correlated trajectory. Upon evoked release of dopamine from a terminal or cluster of terminals, a sharp and localized increase in fluorescence and quick clearance thereafter results in the formation of fluorescence hotspots that travel as a function of distance from the release hotspot. This signal attenuates by diffusion and DAT mediated clearance. Analysis of hot spots over their spatial and temporal trajectories reveals the evolution expected from diffusion of molecules from a point of high concentration and their subsequent reuptake as a function of distance. We calculate a propagation of dopamine signal in the ECS exhibiting a quick attenuation in amplitude of ~60% within a 20 µm distance with a temporal delay in the signal of 2 s at a distance of 70 µm from the hot spot.

Kinetic analysis of nIRDAS fluorescence transients. We analyzed kinetics of dopamine modulation from nIRDA fluorescence for evoked (L-stim, K-stim) and non-evoked activity recordings. For each preparation, we analyzed dopamine reuptake rates over multiple slices in the ECS. The dopamine reuptake kinetic parameter, which we report as the ratio of the reuptake rate $r_{max}$ to the Michaelis constant $K_m$ ($k_{uptake}=r_{max}/K_m$), enabled us to compare dopamine reuptake kinetics based on stimulation method. L-stim and non-evoked dynamics yield fastest dopamine reuptake behavior. In comparison, K-stim slices showed an order of magnitude slower dopamine reuptake, likely a consequence of high concentration of $K^+$ ion on the performance of DATs.

We started with an in-vitro sensor calibration curve modified to account for nanosensor saturation by basal dopamine concentrations ex vivo and in vivo. Michaelis-Menten kinetic behavior for dopamine reuptake enables us to extract the parameter $r_{max}$ for select ROIs from the imaging field of view.

Dopamine reuptake inhibitor nomifensine is a common antidepressant drug marketed under Merital or Alival, and slows the clearance of dopamine from the ECS. Nomifensine competitively binds to dopamine transporters, membrane proteins that mediate the reuptake of dopamine, effectively lowering the affinity parameter between dopamine and dopamine transporters. To further investigate dopamine reuptake kinetics, we performed K-stim and L-stim slice experiments in aCSF solution containing 10 µM nomifensine. Following stimulation, we observe an extended persistence in the fluorescence of nIRDAs, consistent with the anticipated slowdown in dopamine clearance from the ECS. Quantitative analysis of dopamine reuptake kinetics shows that application of nomifensine produced significant slowdown in clearance rates for both L-stim and K-stim slices. While the effect of the nomifensine on dopamine clearance is expected, a closer examination of the clearance profile reveals a surprising presence of two distinct regimes. In the first regime, nIRDA fluorescence falls quickly following dopamine release, as expected for DAT-mediated dopamine clearance. The second dopamine clearance regime follows, in which a sudden transition to slower dopamine reuptake is observed. This phenomenon is consistently observed in all striatal brain slices bathed in nomifensine (10 µM). Our results indicate the existence of two dopamine clearance regimes from the ECS. In the first regime, the diffusive flux out of volume is the predominant means by which dopamine concentration decreases. Dominant diffusive clearance occurs immediately following stimulation and release of dopamine. The dynamics of this regime is governed predominantly by the effective diffusivity of dopamine in the ECS and the relative proximity of the volume of interest to the release site, and is unaffected by the presence of reuptake inhibiting drugs. In the second regime, DAT-mediated clearance is predominant, in which dopamine reuptake dynamics can be manipulated by drugs that interfere with the DAT-DA affinity parameter.

Analyzing the rise rate of nIRDA fluorescence signals further bolsters our hypothesis of the presence of two dopamine clearance regimes. The dopamine concentration rise rate is a function of proximity to the releasing dopaminergic terminal. Signals obtained from ROIs that are proximal to the dopamine-releasing terminal will show higher rise rates compared to ROIs that are located distal to release sites. Rise rates therefore provide a measure of an ROI's proximity to the releasing terminal. If diffusion mediated clearance is an important component of the computed apparent reuptake constant, $k_{uptake}$, its magnitude will show a positive correlation with proximity to dopamine release sites, and importantly, to the rise rate. This positive correlation is indeed apparent for all evoked and non-evoked data we analyzed. To further substantiate our findings, we implemented a stochastic simulation of dopamine neuromodulation in the dorsal striatum in the presence and absence of nomifensine. Our simulation probes the spatial evolution of a single quantal release of dopamine in the presence ($K_m$=8 µM), and absence ($K_m$=0.2 µM) of nomifensine, and reveals that the clearance of dopamine exhibits dual behavior at distances close to the releasing terminal. The model predicts that close to the releasing terminal the diffusive clearance of dopamine is the dominant process, and thus nomifensine minimally affects the reuptake of dopamine Conversely, in the absence of nomifensine, our model recovers the quick DAT-mediated dopamine reuptake behavior we observe in nomifensine-free slice experiments. Our results illuminate two dopamine reuptake clearance regimes in the presence of a DAT-mediated reuptake inhibitor, regimes likely not observed in data from FSCV measurements in which the spatial profile of dopamine release is averaged over hundreds of termini.

The invention claimed is:

1. A method of imaging in mammalian brain tissue comprising: detecting changes in extracellular concentration of a neurotransmitter with a sensor located in live brain tissue in a brain slice or live mammal, the sensor comprising a functionalized, neurocompatible single-walled carbon nanotube (SWNT) comprising an adsorbed neurotransmitter-selective polynucleotide covalently bound to a neurocompatible polyethyleneglycol (PEG), wherein the polynucleotide is $(GT)_6$, wherein the sensor exhibits detectably greater fluorescence in the presence of the neurotransmitter than in the absence thereof, and the sensor responds to the neurotransmitter on a millisecond time scale.

2. The method of claim 1 wherein the brain tissue is in a live mammal.

3. The method of claim 1 further comprising generating optical imaging of spatial distribution, concentration, and dynamics of the neurotransmitter in real time.

4. The method of claim 2 further comprising generating optical imaging of spatial distribution, concentration, and dynamics of the neurotransmitter in real time.

5. The method of claim 1 further comprising delivering the sensor to the mammal by injection.

6. The method of claim 2 further comprising delivering the sensor to the mammal by injection.

7. The method of claim 3 further comprising delivering the sensor to the mammal by injection.

8. The method of claim 1 wherein the neurotransmitter is selected from epinephrine (adrenaline), norepinephrine (noradrenaline), dopamine, 5-hydroxytryptamine (serotonin), glutamic acid, L-3,4-dihydroxyphenylalanine (L-dopa), 3,4-Dihydroxyphenylacetic acid (DOPAC), homovannilic acid and tyramine.

9. The method of claim 2 wherein the neurotransmitter is selected from epinephrine (adrenaline), norepinephrine (noradrenaline), dopamine, 5-hydroxytryptamine (serotonin), glutamic acid, L-3,4-dihydroxyphenylalanine (L-dopa), 3,4-Dihydroxyphenylacetic acid (DOPAC), homovannilic acid and tyramine.

10. The method of claim 3 wherein the neurotransmitter is selected from epinephrine (adrenaline), norepinephrine (noradrenaline), dopamine, 5-hydroxytryptamine (serotonin), glutamic acid, L-3,4-dihydroxyphenylalanine (L-dopa), 3,4-Dihydroxyphenylacetic acid (DOPAC), homovannilic acid and tyramine.

11. The method of claim 1 wherein the neurotransmitter is dopamine.

12. The method of claim 2 wherein the neurotransmitter is dopamine.

13. The method of claim 3 wherein the neurotransmitter is dopamine.

14. The method of claim 4 wherein the neurotransmitter is dopamine.

15. The method of claim 5 wherein the neurotransmitter is dopamine.

16. The method of claim 6 wherein the neurotransmitter is dopamine.

17. The method of claim 7 wherein the neurotransmitter is dopamine.

18. The method of claim 1 wherein the neurotransmitter is norepinephrine.

19. The method of claim 2 wherein the neurotransmitter is norepinephrine.

20. The method of claim 3 wherein the neurotransmitter is norepinephrine.

* * * * *